(12) United States Patent
Lang et al.

(10) Patent No.: US 8,071,704 B2
(45) Date of Patent: Dec. 6, 2011

(54) PREPOLYMERIZABLE SURFACE ACTIVE MONOMERS WITH BOTH FLUORINE-CONTAINING GROUPS AND HYDROPHILIC GROUPS

(75) Inventors: Weihong Lang, Amston, CT (US); Yu-Chin Lai, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 466 days.

(21) Appl. No.: 12/241,102

(22) Filed: Sep. 30, 2008

(65) Prior Publication Data

US 2009/0092655 A1    Apr. 9, 2009

Related U.S. Application Data

(60) Provisional application No. 60/977,129, filed on Oct. 3, 2007.

(51) Int. Cl.
C08F 214/18    (2006.01)
C08L 27/12    (2006.01)
G02B 1/04    (2006.01)

(52) U.S. Cl. ........ 526/292.2; 526/248; 526/279; 526/292.1; 526/292.6; 424/429; 623/6.56; 560/172; 560/223

(58) Field of Classification Search .......... 560/172, 560/223; 526/248, 279, 292.1, 292.95, 303.1; 523/106, 107; 424/429; 623/6.56
See application file for complete search history.

(56) References Cited

U.S. PATENT DOCUMENTS

| | | | |
|---|---|---|---|
| 3,408,429 A | 10/1968 | Wichterle | |
| 3,496,254 A | 2/1970 | Wichterle | |
| 4,084,459 A | 4/1978 | Clark | |
| 4,136,250 A | 1/1979 | Mueller et al. | |
| 4,153,641 A | 5/1979 | Deichert et al. | |
| 4,192,827 A | 3/1980 | Mueller et al. | |
| 4,197,266 A | 4/1980 | Clark et al. | |
| 4,486,577 A | 12/1984 | Mueller et al. | |
| 4,547,459 A * | 10/1985 | Kamio et al. | 430/631 |
| 4,605,712 A | 8/1986 | Mueller et al. | |
| 4,740,533 A | 4/1988 | Su et al. | |
| 4,859,349 A * | 8/1989 | Clark et al. | 252/3 |
| 4,910,277 A | 3/1990 | Bambury et al. | |
| 4,954,587 A | 9/1990 | Mueller | |
| 5,034,461 A | 7/1991 | Lai et al. | |
| 5,070,215 A | 12/1991 | Bambury et al. | |
| 5,260,000 A | 11/1993 | Nandu et al. | |
| 5,271,875 A | 12/1993 | Appleton et al. | |
| 5,310,779 A | 5/1994 | Lai | |
| 5,358,995 A | 10/1994 | Lai et al. | |
| 5,374,662 A | 12/1994 | Lai et al. | |
| 5,420,324 A | 5/1995 | Lai et al. | |
| 5,496,871 A | 3/1996 | Lai et al. | |

FOREIGN PATENT DOCUMENTS

| | | |
|---|---|---|
| EP | 0103274 | 3/1984 |
| EP | 0524557 A1 | 1/1993 |

OTHER PUBLICATIONS

Machine Translation of Description of DE 3233830 (Mar. 15, 1984).*
STN structure search results (Jan. 24, 2011).*
International Search Report (PCT/ISA/210) and Written Opinion (PCT/ISA/237) mailed on Dec. 23, 2008.

* cited by examiner

*Primary Examiner* — David W Wu
*Assistant Examiner* — Vu A Nguyen
(74) *Attorney, Agent, or Firm* — Glenn D. Smith

(57) ABSTRACT

Provided are surface modified contact lenses formed from one or more fumaric- or itaconic-containing prepolymers having reactive functionality that is complimentary to surface modifying polymers.

18 Claims, 1 Drawing Sheet

PREPOLYMERIZABLE SURFACE ACTIVE MONOMERS WITH BOTH FLUORINE-CONTAINING GROUPS AND HYDROPHILIC GROUPS

CROSS-REFERENCE TO RELATED APPLICATIONS

This application claims the benefit of Provisional Patent Application No. 60/977,129 filed Oct. 3, 2007 which is incorporated by reference herein.

FIELD OF THE INVENTION

The present invention relates generally to reactive fumaric-, maleic- and itaconic-containing fluorinated prepolymers and compositions comprising the prepolymers used in the manufacture of medical devices. More specifically, the present invention relates to contact lenses formed from one or more fluorinated fumaric-, maleic- or itaconic-containing prepolymers.

BACKGROUND OF THE INVENTION

Medical devices such as ophthalmic lenses made from silicone materials have been investigated for a number of years. Such materials can generally be sub-divided into two major classes, namely hydrogels and non-hydrogels. Non-hydrogels do not absorb appreciable amounts of water, whereas hydrogels can absorb and retain water in an equilibrium state. Hydrogels generally have water content between about 15 to about 80 weight percent. Regardless of their water content, both non-hydrogel and hydrogel silicone medical devices tend to have relatively hydrophobic, non-wettable surfaces that have a high affinity for lipids. This problem is of particular concern with contact lenses.

Fumarate- and fumaramide-containing monomers and compositions comprising the monomers have been developed to make highly oxygen permeable hydrogels which may be used to make biomedical devices including contact lenses. Examples of these fumarate- and fumaramide-containing monomers and compositions can be found in U.S. Pat. Nos. 5,374,662, 5,420,324, and 5,496,871, the contents of each being incorporated by reference herein. Because of the polar character of amide functionality, this class of monomer shows good compatibility with both hydrophobic monomers such as tris (trimethylsiloxy) silane (TRIS) and hydrophilic monomers such as N,N-dimethylacrylamide (DMA). These prior art prepolymers provide silicone hydrogels with excellent oxygen permeability and mechanical properties. However, like other silicone hydrogels, they are not wettable enough to be useful as continuous wear lenses unless the surface is treated.

Surface structure and composition determine many of the physical properties and ultimate uses of solid materials. Characteristics such as wettability and lipid deposit resistance are largely influenced by surface characteristics. The alteration of surface characteristics is of special significance in biotechnical applications where biocompatibility is of particular concern. Therefore, those skilled in the art have long recognized the need for rendering the surface of contact lenses and other medical devices hydrophilic or more hydrophilic. Increasing the hydrophilicity of the contact-lens surface improves the wettability of the contact lenses with tear fluid in the eye. This in turn improves the wear comfort of the contact lenses. In the case of continuous-wear lenses, the surface is especially important. The surface of a continuous-wear lens must be designed not only for comfort, but to avoid adverse reactions such as corneal edema, inflammation, or lymphocyte infiltration. Improved surface active monomers have accordingly been sought for preparing contact lenses having improved surface properties.

SUMMARY OF THE INVENTION

Provided herein are novel polymerizable surface active monomers with both fluorine-containing groups and amine groups. The monomers have the structure of formulae (I), (II) and (III) below.

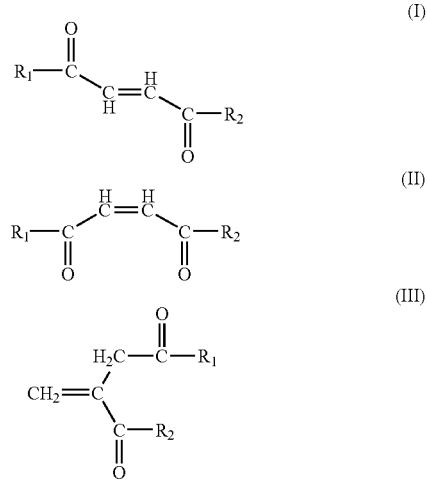

wherein $R_1$ is O—Rf or NH—Rf, Rf is an alkyl group of 4 to 20 carbon atoms containing fluorine atoms; and $R_2$ is an amino-containing alkyl group of 1 to 10 carbon atoms.

A preferred monomer has the following formula (IV):

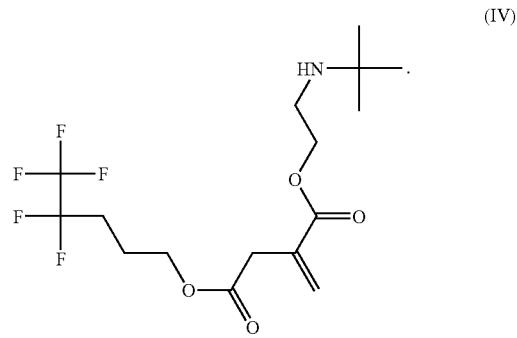

Also provided are polymerized monomer mixtures of formulae (I), (II) and (III) and devices comprising polymerized monomer mixtures comprising monomers of formulae (I), (II) and (III).

Also provided is a surface modified medical device comprising a medical device manufactured from a monomer mixture containing a surface-active fluorinated prepolymer containing an amino group.

DETAILED DESCRIPTION OF THE INVENTION

Figure 1:
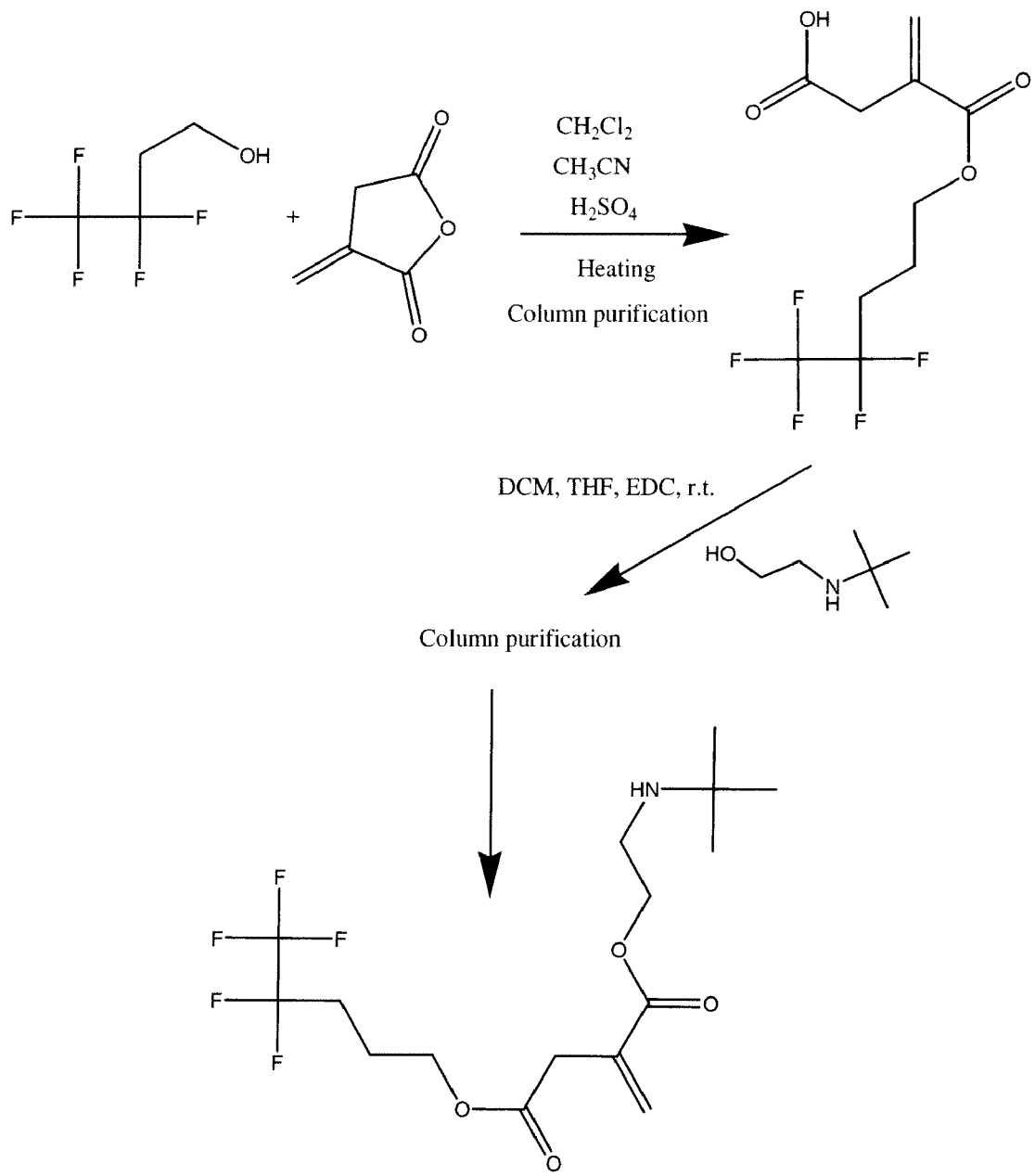
FIG. 1 is a representative synthetic method of making a prepolymer of the invention herein.

The present invention is directed toward reactive fumaric-, maleic- and itaconic-containing fluorinated prepolymers for use with copolymerizable polymeric systems used for biomedical devices, especially contact lenses. As used herein, fumaric refers to a derivative of fumaric acid and can be a fumarate (an ester), a fumaramide (an amide) or a residue having both ester and amide functionalities. The fumaric group is a residue of trans-1,2-ethylenedicarboxylate. Therefore, it will be understood that the diastereoisomer of fumarate, maleate, is also intended to be included in the fumaric-containing prepolymers of the present invention. Itaconic refers to derivatives of itaconic acid and has a similar meaning as that of fumaric. In further embodiments of the present invention, the prepolymers are used to make biomedical devices and are useful in contact lens formulations which may be either "soft" or "hard" and which may preferably be hydrogels.

The reactive fumaric-, maleic- and itaconic-containing fluorinated prepolymers of the present invention have at least one fumaric, maleic or itaconic group. Monomer mixes comprising the prepolymers of the present invention may comprise both thermal- and photoinitiators for curing purposes. The monomer mixes may further comprise at least one hydrophilic monomer. Further, the monomer mix may additionally comprise at least one silicone monomer.

When the term "reactive" is used herein we refer to the ability to modify the lens surface through amino groups residing on the lens surface and available for post treatment of the lens.

As is known in the field, certain crosslinked polymeric materials may be polymerized to form a hard, water-free, xerogel. Xerogels are understood to be unhydrated hydrogel formulations. It was found that such xerogels could be physically altered to, for example, impart optical properties through machining, and then be hydrated and retain their water content.

When the term "polymerization" or "polymerizable" is used herein we refer to the polymerization of the double bonds or acrylic group of the monomers and prepolymers with polymerizable unsaturated groups which results in a crosslinked three-dimensional network.

Further, notations such as "(meth) acrylate" or "(meth) acrylamide" are used herein to denote optional methyl substitution. Thus, for example, (meth)acrylate includes both acrylate and methacrylate and N-alkyl-(meth)acrylamide includes both N-alkyl acrylamide and N-alkyl methacrylamide.

The term "prepolymer" denotes a high molecular weight monomer containing polymerizable groups. The monomers added to the monomeric mixture of the present invention may therefore be low molecular weight monomers or prepolymers. Thus, it is understood that a term such as "silicone monomers" includes "silicone prepolymers" as well as "silicone macromers".

The terms "shaped articles for use in biomedical applications" or "biomedical devices or materials" or "biocompatible materials" mean the hydrogel materials disclosed herein have physicochemical properties rendering them suitable for prolonged contact with living tissue, blood and the mucous membranes.

While the present invention contemplates the use of reactive fumaric-, maleic- and itaconic-containing fluorinated prepolymers for medical devices including both "hard" and "soft" contact lenses, the formulations containing the reactive fumaric-, maleic- and itaconic-containing fluorinated prepolymers of the present invention are thought to be especially useful as soft hydrogel contact lenses. As is understood in the field, a lens is considered to be "soft" if it can be folded back upon itself without breaking.

A hydrogel is a hydrated cross-linked polymeric system that contains water in an equilibrium state. Silicone hydrogels (i.e., hydrogels containing —OSi— linkages) are usually prepared by polymerizing a mixture containing at least one silicone monomer and at least one hydrophilic monomer. By the term silicone, it is meant that the material is an organic polymer comprising at least five percent by weight silicone, preferably 10 to 100 percent by weight silicone, more preferably 30 to 90 percent by weight silicone. Applicable silicone monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Provided herein are novel reactive fumaric-, maleic- and itaconic-containing fluorinated prepolymers. The monomers have the structure of formulae (I), (II) and (III) below:

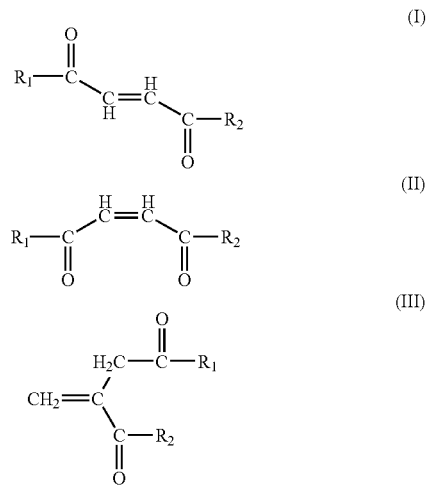

wherein $R_1$ is O—Rf or NH—Rf, Rf is an alkyl group of 4 to 20 carbon atoms containing fluorine atoms; and $R_2$ is an amino-containing alkyl group of 1 to 10 carbon atoms.

The reactive fumaric-, maleic- and itaconic-containing fluorinated prepolymers of the present invention have at least one fumaric, maleic or itaconic group.

A preferred monomer has the following formula (IV):

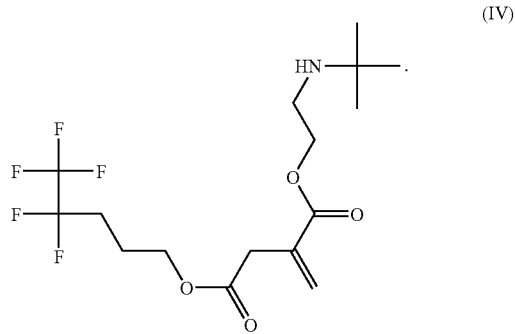

Also provided are polymerized monomer mixtures of formulae (I), (II) and (III) and devices comprising polymerized monomer mixtures comprising monomers of formulae (I), (II) and (III).

Monomer mixes comprising the prepolymers of the present invention may comprise at least one hydrophilic monomer. The monomer mixes may further comprise at least one silicone monomer. Further, the monomer mix may additionally comprise thermal- and/or photoinitiators for curing purposes.

The reactive fumaric-, maleic- and itaconic-containing fluorinated prepolymers of the present invention (i.e., reactive surface active monomers) are prepared according to syntheses well known in the art and according to the examples disclosed herein. The reactive fumaric-, maleic- and itaconic-containing fluorinated prepolymers of the present invention are incorporated into the monomer mix. The relative weight % of the reactive fumaric-, maleic- and itaconic-containing fluorinated prepolymers as compared to the total monomer mix weight % is from about 0.01 to about 10%, more preferably from about 0.1% to about 5%, and most preferably about 0.2% to about 1%.

Examples of hydrophilic monomers include, but are not limited to, ethylenically unsaturated lactam-containing monomers such as N-vinyl pyrrolidinone; methacrylic and acrylic acids; (meth)acrylic substituted alcohols, such as 2-hydroxyethylmethacrylate (HEMA) and 2-hydroxyethylacrylate; and (meth)acrylamides, such as methacrylamide and N,N-dimethylacrylamide (DMA); vinyl carbonate or vinyl carbamate monomers such as disclosed in U.S. Pat. No. 5,070,215; and oxazolinone monomers such as disclosed in U.S. Pat. No. 4,910,277. Other hydrophilic monomers such as glycerol methacrylate and polyethyleneglycol monomethacrylate are also useful in the present invention.

Preferred hydrophilic vinyl-containing monomers that may be incorporated into the hydrogels of the present invention include monomers such as N-vinyl lactams such as N-vinyl pyrrolidinone (NVP), N-vinyl-N-methyl acetamide, N-vinyl-N-ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred. Other suitable hydrophilic monomers will be apparent to one skilled in the art. The relative weight % of hydrophilic monomer(s) to total weight % of the comonomer mix is preferably from about 5% to 80%, more preferably from about 20% to 70%, and most preferably 20% to 40%.

As mentioned previously, additional silicone monomers may be present in the monomer mixes with the polymerizable fumaric-, maleic or itaconic-containing fluorinated prepolymers of the present invention. One preferred class of suitable silicone monomers which may be incorporated into a monomer mix with the polymerizable fumaric-, maleic- or itaconic-containing fluorinated prepolymers of the present invention are the bulky polysiloxanylalkyl (meth)acrylic monomers represented by the following Formula (IV):

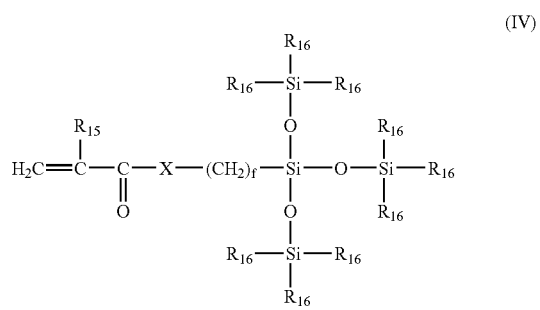

wherein: X is O or NR; R is an alkyl group having 1 to 5 carbon atoms; each $R_{15}$ is independently hydrogen or an alkyl group having 1 to 10 carbon atoms; each $R_{16}$ is independently a lower alkyl having 1 to 5 carbon atoms or a phenyl group; and f is 1 or 3 to 10.

Such bulky monomers include methacryloxypropyl tris(trimethylsiloxy)silane (TRIS), pentamethyldisiloxanylmethylmethacrylate, tris(trimethylsiloxy)methacryloxy propylsilane, phenyltetramethyldisiloxanylethyl acrylate, and methylbis(trimethylsiloxy)methacryloxymethyl silane. Further preferred classes of silicone monomers which may be incorporated into a monomer mix with the polymerizable fumaric-, maleic- or itaconic-containing fluorinated monomers of the present invention are the poly(organosiloxane) monomers represented by the following formula (V):

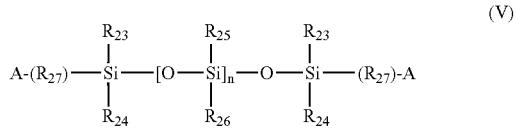

wherein: A is an activated unsaturated group, such as an ester or amide of an acrylic or a methacrylic acid; each $R_{23}$-$R_{26}$ is independently selected from the group consisting of a monovalent hydrocarbon radical or a halogen substituted monovalent hydrocarbon radical having 1 to 18 carbon atoms which may have ether linkages between carbon atoms; $R_{27}$ is a divalent hydrocarbon radical having from 1 to 22 carbon atoms and may contain ether or thio linkage; and n is 0 or an integer greater than or equal to 1. When siloxane-containing monomers other than the bulky silicone prepolymers are incorporated into the monomer mix, the weight % of the other siloxane-containing monomers as compared to the total monomer mix weight % is from about 1% to 60%, more preferably from about 3% to 50%, and most preferably 5% to 40%.

Either the silicone monomer, the reactive fumaric-, maleic- or itaconic-containing fluorinated prepolymer, or the hydrophilic monomer may function as a crosslinking agent (a crosslinker), being defined as a monomer having multiple polymerizable functionalities. Additional crosslinkers also may be present in the monomer mix which polymerizes to form the hydrogel.

Most "known" crosslinking agents are hydrophobic. When it is desirable for both an acrylic-containing monomer and a vinyl-containing monomer to be incorporated into the silicone polymer of the present invention, a further crosslinking agent having both a vinyl and an acrylic polymerizable group may be used, since these vinyl and acrylic monomers have differing reactivity ratios and may not copolymerize efficiently. Such crosslinkers which facilitate the copolymerization of these monomers are the subject of U.S. Pat. No. 5,310,779, the content of which is incorporated herein by reference. Such crosslinkers are represented by the following schematic representation:

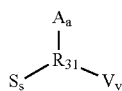

wherein V denotes a vinyl-containing group having the formula:

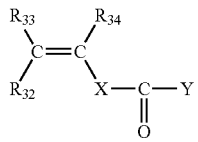

A denotes an acrylic-containing group having the formula:

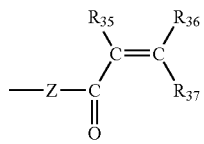

and S denotes a styrene-containing group having the formula:

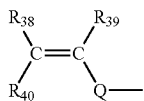

wherein $R_{31}$ is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups; $R_{32}$-R40 are independently H, or alkyl of I to 5 carbon atoms; Q is an organic group containing aromatic moieties having 6-30 carbon atoms; X, Y, and Z are independently O, NH or S; v is 1, or higher; and a and s are independently greater than or equal to 0; and a+s is greater than or equal to 1. An example is 2-hydroxyethyl-methacrylate vinyl carbonate or carbamate.

Other crosslinking agents which may be incorporated into the silicone hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentaerythritol, butylene glycol, mannitol, and sorbitol. Further examples include N,N-methylene-bis-(meth) acrylamide, sulfonated divinylbenzene, and divinylsulfone. Also useful are the reaction products of hydroxyalkyl (meth) acrylates with unsaturated isocyanates, for example the reaction product of 2-hydroxyethyl methacrylate with 2-isocyanatoethyl methacrylate (IEM). See U.S. Pat. No. 4,954,587.

Other known crosslinking agents are polyether-bisurethane-dimethacrylates (see U.S. Pat. No. 4,192,827), and those crosslinkers obtained by reaction of polyethylene glycol, polypropylene glycol and polytetramethylene glycol with 2-isocyanatoethyl methacrylate (IEM) or m-isopropenyl-γ,γ-dimethylbenzyl isocyanates (m-TMI), and polysiloxane-bisurethane-dimethacrylates. See U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

The prepolymers of the present invention, when copolymerized, are readily cured to cast shapes by methods such as UV polymerization, use of free radical thermal initiators and heat, or combinations thereof. Representative free radical thermal polymerization initiators are organic peroxides, such as for example acetyl peroxide, lauroyl peroxide, decanoyl peroxide, stearoyl peroxide, benzoyl peroxide, tertiary butyl peroxypivalate, peroxydicarbonate, and the commercially available thermal initiators such as LUPERSOL® 256, 225 (Atofina Chemical, Philadelphia, Pa.) and the like, employed in a concentration of about 0.01 to 2 percent by weight of the total monomer mixture. Representative UV initiators are those known in the field such as, benzoin methyl ether, benzoin ethyl ether, DAROCUR®-1173, 1164, 2273, 1116, 2959, 3331, IGRACURE® 651 and 184 (Ciba Specialty Chemicals, Ardsley, N.Y.).

In addition to the above-mentioned polymerization initiators, the copolymer of the present invention may also include other components as will be apparent to one skilled in the art. For example, the monomer mix may include additional colorants, or UV-absorbing agents and toughening agents such as those known in the contact lens art.

The resulting copolymers of this invention can be formed into contact lenses by the spincasting processes such as those disclosed in U.S. Pat. Nos. 3,408,429 and 3,496,254, static casting processes such as in U.S. Pat. No. 5,271,875 and other conventional methods, such as compression molding as disclosed in U.S. Pat. Nos. 4,084,459 and 4,197,266.

Polymerization of the monomer mix may be conducted either in a spinning mold, or a stationary mold corresponding to a desired contact lens shape. The thus-obtained contact lens may be further subjected to a mechanical finishing, as occasion demands. Also, the polymerization may be conducted in an appropriate mold or vessel to give a lens material in the form of a button, plate or rod, which may then be processed (e.g., cut or polished via lathe or laser) to give a contact lens having a desired shape.

In certain embodiments, the hydrogels produced by the present invention are oxygen permeable, hydrolytically stable, biologically inert, and transparent. The monomers and prepolymers employed in accordance with this invention are readily polymerized to form three-dimensional networks which permit the transport of oxygen and, in certain embodiments, are optically clear, strong and hydrophilic.

The present invention provides materials which can be usefully employed for the fabrication of prostheses such as heart valves and intraocular lenses, as optical contact lenses or as films. More particularly, the present invention concerns contact lenses.

The present invention further provides articles of manufacture which can be used for biomedical devices, such as, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices and especially contact lenses.

It is known that blood, for example, is readily and rapidly damaged when it comes into contact with artificial surfaces. The design of a synthetic surface which is antithrombogenic and nonhemolytic to blood is necessary for prostheses and devices used with blood.

Although the teachings of the present invention are preferably applied to soft or foldable contact lenses or like medical devices formed of a foldable or compressible material, the same may also be applied to harder, less flexible, lenses formed of a relatively rigid material such as poly(methyl methacrylate) (PMMA).

The reactive fumaric-, maleic- and itaconic-containing fluorinated prepolymers useful in certain embodiments of the present invention may be prepared according to syntheses well known in the art and according to the methods disclosed in the following examples.

ABBREVIATIONS

NVP 1-Vinyl-2-pyrrolidone
TRIS Methacryloxypropyltris(trimethylsiloxy)silane
HEMA 2-Hydroxyethyl methacrylate
HEMAVC 2-methacryloxyethyl vinyl carbonate
HEMA-TMS 2-Trimethylsiloxyethyl methacrylate trimethylsilyl
Vazo 64 2,2'-Azobis(2-methylpropionitrile)
EGDMA Ethylene glycol dimethacrylate
SA 2-[3-(2H-Benzotriazol-2-yl)-4-hydroxyphenyl]ethyl methacrylate
IMVT 1,4-bis[4-(2-methacryloxyethyl)phenylamino]anthraquinone
PFPBAEM 4,4,5,5,5-pentafluoropentyl t-butylaminoethyl itaconate Unless otherwise specifically stated or made clear by its usage, all numbers used in the examples should be considered to be modified by the term "about" and to be weight percent.

EXAMPLES

Example 1

Preparation of 4,4,5,5,5,-PENTAFLUOROPENTYL ITACONIC ACIDE

In an oven-dried 250 ml round bottom flask was added, under the flushing of dry nitrogen; Itaconic anhydride, 12.236 g (109.16 mmol), methylene chloride 60 ml, acetonitrile 120 ml, 4,4,5,5,5-pentafluoropentanol 19.653 g (110.35 mmol), concentrated sulfuric acid 30 drops. The reaction mixture was refluxed at 60° C. overnight. After silica gel column purification 4,4,5,5,5-pentafluoropentanol itaconic acid was obtained. The proposed structure was confirmed by NMR and GC MS etc.

NMR and MS

NMR: $^1$H: 1.858 ppm, quintuplet; 1.938 ppm, multiplet; 2,084 ppm, multiplet; 3.344 ppm, singlet; 3.769, multiplet; 4.176 ppm, triplet; 5.831 ppm, singlet; 6.461 ppm, singlet; 11.650 ppm, broad:

$^{13}$C: 20.246 ppm, singlet; 25.768 ppm, singlet; 27.696 ppm, triplet; 37.483 ppm, singlet; 63.606 ppm, singlet; 68.096 ppm, singlet; 115.681 ppm, singlet; 116.049 ppm, singlet; 131.136 ppm, singlet; 133.359 ppm, singlet; 170.621 ppm, singlet; 171.642 ppm, singlet.

GC MS: predominant peak at 6.3 minute, $M^+$=290, fragments confirm the structure, 161, 130, 113, 85; 47

ESI MS: $M/Na^+$=313.01

Example 2

Preparation of 4,4,5,5,5,-PENTAFLUOROPENTYL T-BUTYLAMINOETHYL ITACONATE

To an oven-dried 250 ml three-neck flask under the flushing of dry nitrogen was added 4,4,5,5,5,-pentafluoropentyl itaconic acid 6.5 g (22.399 mmol), anhydrous methylene chloride, 110 ml, anhydrous THF 6 ml and 1-ethyl-3-(3-dimethylaminopropyl)-carbodimide (EDC) 4.566 g (23.818 mmol). To the stirring solution was added tert-butylamino ethanol 2.83 g (24.149 mmol), and stirred at room temperature over the weekend.

After silica gel column purification about 2.76 g product was recovered. NMR, GC-MS and ESI-MS and were used for characterization.

NMR $^{13}$C: 20.0 ppm, singlet; 27.9 ppm, triplet; 29.069, singlet; 30.2 ppm, singlet; 37.940 ppm, singlet; 41.3 ppm, singlet 50.492 ppm, singlet; 63.3 ppm, singlet; 66.0 ppm, singlet; 129.1 ppm, singlet; 13.9 ppm, singlet; 166.113 ppm, singlet; 170.69 ppm, singlet;

$^1$H: 0.869 ppm triplet, 1,100 ppm, singlet; 1.254 ppm, singlet; 1.419 ppm, singlet; 1.602 ppm, broad singlet; 1.913-1.967, multiplet; 2.043-2.132, multiplet; 2.839 ppm triplet; 3.345 ppm, singlet; 4.165 ppm triplet; 4.246 ppm triplet; 5.716 ppm doublet; 6.329 ppm doublet.

ESI MS: $M/H^+$=390.189, $M/Na^+$=412.179

GC MS: predominant peak at 7.5 minute, $M^+$=389

Example 3

Preparation of Urethane Prepolymer

A dry three neck 500 ml round bottom flask was connected to a nitrogen inlet tube and a reflux condenser. The following were added to the flask all at once: isophorone diisocyanate (23.149 g, 104.139 mmol); α,ω-bis (4-hydroxybutyl)-polydimethylsiloxane (208.54 g, 51.568 mmol); dibutyl tin dilaurate (0.690 g); 400 ml methylene chloride. The contents were refluxed overnight. Diethyleneglycol (4.769 g, 44.940 mmol) was then added and refluxed overnight again. Then the contents were cooled down to ambient temperature. 1,1' bi 2 naphthol (0.032 g) and 2 hydroxyethyl methacrylate (1.751 g, 13.455 mmol) were added and stirred until the isocyanate peak at 22.67 $cm^{-1}$ disappeared from IR spectrum of the product. The solvent was then stripped under reduced pressure to yield liquid product.

Example 4

Preparation of Monomer Mix for Silicone Hydrogel Lens

The following formulation was used in lens casting, with the presence of 2 parts of 4,4,5,5,5-pentafluoropentyl t-butylaminoethyl itaconate (PFPBAEM):

| FORMULATION: | PARTS BY WEIGHT |
|---|---|
| Monomer of Ex. 3 | 53 |
| TRIS | 15 |
| HEMA | 5 |
| NVP | 33 |
| HEMAVC | 1 |
| n-Hexanol | 10 |
| Vazo 64 | 0.5 |
| PFPBAEM | 2 |
| IMVT | 150 ppm |
| Total Parts | 119.5 |
| Clarity of mix | Clear |
| Lens clarity | Clear |

Example 5

Manufacturing of Silicone Hydrogel Lenses

The monomer mix of Example 4 was cast into polypropylene molds and cured under UV for 90 minutes. After opening the mold, it was found that 99% (58/59) of lenses stayed with anterior molds. They were then extracted with ispropanol and then placed in DI water.

Example 6

Comparative

A formulation, which was the same as that of Example 4 except no PFPBAEM was added. After the same lens casting process, it was found that 90% (52/58) of lenses stayed with the anterior half. This suggested that the presence of fluorine improved the preferential stay of lenses after molds opened.

Example 7

Surface Analysis of Silicone Hydrogel Lenses

Lenses were dried and sent for surface analysis. Contact angels are measured.

Example 8

Surface Modification of Silicone Hydrogel Lenses

Lenses from Example 4 are placed into glass vials and then filled with 3% of poly(GM-co-AA) and then autoclaved for 1 cycle. Lenses are then washed with DI water; dried lenses are then analyzed for contact angles. It is found that the contact angels dropped from about 110° for control to below 90° for treated.

Contact lenses manufactured using the unique materials of the present invention are used as customary in the field of ophthalmology. While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

What is claimed is:

1. A reactive surface active monomer having the structure below:

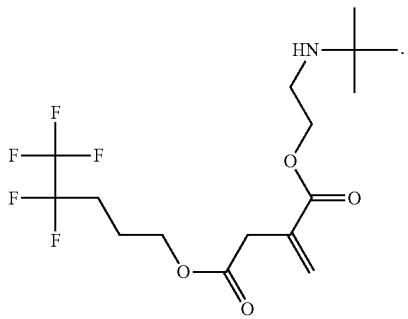

2. A polymerizable monomer mixture comprising at least one monomer of claim 1.

3. The polymerizable monomer mixture of claim 2 wherein a relative weight % of the polymerizable surface active monomer as compared to the total monomer mix weight % is from about 0.01% to about 10%.

4. The polymerizable monomer mixture of claim 2 wherein a relative weight % of the polymerizable surface active monomer as compared to the total monomer mix weight % is about 0.1% to about 5%.

5. The polymerizable monomer mixture of claim 2 wherein a relative weight % of the polymerizable surface active monomer as compared to the total monomer mix weight % is about 0.2% to about 1%.

6. The monomer mixture of claim 2 further comprising at least one hydrophilic monomer.

7. The monomer mixture of claim 6 wherein the hydrophilic monomer is selected from the group consisting of ethylenically unsaturated lactam-containing monomers, methacrylic acids, acrylic acids, (meth)acrylic substituted alcohols, (meth)acrylamides, vinyl carbonate, vinyl carbamate monomers, oxazolinone monomers, glycerol methacrylate, polyethyleneglycol monomethacrylate and mixtures thereof.

8. The monomer mixture of claim 2 further comprising at least one silicone monomer.

9. The monomer mixture of claim 8 wherein the at least one silicone monomer is a bulky polysiloxanylalkyl (meth)acrylic monomer.

10. The monomer mixture of claim 8 wherein the at least one silicone monomer is selected from the group consisting of methacryloxypropyl tris(trimethylsiloxy)silane (TRIS), pentamethyldisiloxanylmethylmethacrylate, tris(trimethylsiloxy)methacryloxy propylsilane, phenyltetramethyldisiloxanylethyl acrylate, methylbis(trimethylsiloxy)methacryloxymethyl silane and mixtures thereof.

11. The monomer mixture of claim 2 further comprising a crosslinking agent.

12. A surface modified medical device comprising a medical device manufactured from a monomer having the structure below:

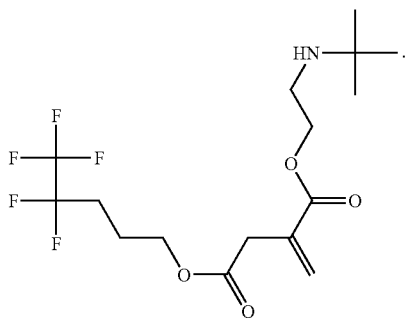

13. The medical device of claim 12 wherein the medical device has at least one of the property selected from the group consisting of oxygen permeability, hydrolytically stability, biologically inertness, and transparency.

14. The medical device of claim 12 wherein the medical device has a three-dimensional networks which permits the transport of oxygen.

15. The medical device of claim 12 wherein the medical device is an optically clear, strong and hydrophilic medical device.

16. The medical device of claim 15 wherein the medical device is an ophthalmic lens.

17. The medical device of claim 16 wherein the medical device is a contact lens.

18. The medical device of claim 16 wherein the medical device is an intraocular lens.

* * * * *